US008916175B2

(12) United States Patent
Cohen et al.

(10) Patent No.: US 8,916,175 B2
(45) Date of Patent: Dec. 23, 2014

(54) SAFER ATTENUATED VARICELLA-ZOSTER VIRUS VACCINES WITH MISSING OR DIMINISHED LATENCY OF INFECTION

(75) Inventors: Jeffrey I. Cohen, Silver Spring, MD (US); Edward M. Cox, Jr., Silver Spring, MD (US); Lesley M. Pesnicak, Stafford, VA (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 2052 days.

(21) Appl. No.: 11/630,147

(22) PCT Filed: Jun. 22, 2005

(86) PCT No.: PCT/US2005/021788
§ 371 (c)(1),
(2), (4) Date: Jan. 3, 2008

(87) PCT Pub. No.: WO2006/012092
PCT Pub. Date: Feb. 2, 2006

(65) Prior Publication Data
US 2008/0279886 A1 Nov. 13, 2008

Related U.S. Application Data

(60) Provisional application No. 60/583,399, filed on Jun. 29, 2004.

(51) Int. Cl.
*A61K 39/25* (2006.01)
*A01N 63/00* (2006.01)
*C12N 7/00* (2006.01)
*C12N 7/04* (2006.01)

(52) U.S. Cl.
CPC ....... *A61K 39/25* (2013.01); *C12N 2710/16761* (2013.01); *C12N 7/00* (2013.01); *C12N 2710/16734* (2013.01)
USPC .................. 424/230.1; 424/93.6; 435/236

(58) Field of Classification Search
CPC ........... A61K 39/25; A61K 2039/5254; A61K 39/245; C12N 2710/16734; C12N 2710/16761; C12N 7/00; C12N 15/86; C12N 2710/16022; C12N 2710/16722; C12N 2710/16743; C12N 2710/16711; C07K 14/005
See application file for complete search history.

(56) References Cited

U.S. PATENT DOCUMENTS

| | | | |
|---|---|---|---|
| 3,985,615 | A | 10/1976 | Kubo |
| 5,728,386 | A | 3/1998 | Provost et al. |
| 6,039,958 | A | 3/2000 | Koyama et al. |
| 6,051,238 | A | 4/2000 | Volkin et al. |
| 6,210,683 | B1 | 4/2001 | Burke et al. |
| 6,258,362 | B1 | 7/2001 | Loudon et al. |
| 6,427,517 | B1 | 8/2002 | McMillan |

FOREIGN PATENT DOCUMENTS

WO WO 2004/042031 5/2004

OTHER PUBLICATIONS

Sommer et al., Journal of Virology, 2001, 75(17):8224-8239.*
Debrus et al., "Varicella-zoster virus gene 63 encodes an immediate-early protein that is abundantly expressed during latency", *J. Virol.* 69:3240-3245 (1995).
Fowler et al., "ORF73 of murine herpesvirus-68 is critical for the establishment and maintenance of latency", *Journal of General Virology* 84(Pt. 12):3405-3416 (2003).
Fowler et al., "Vaccine potential of a murine gammaherpesvirus-68 mutant deficient for ORF73", *The Journal of General Virology* 85(Pt. 3):609-613 (2004).
Fuchs et al., "Characterization of the replication origin (Oris) and adjoining parts of the inverted repeat sequences of the pseudorabies virus genome", *J. Gen. Virol.* 81: 1539-1543 (2000).
Ghiasi et al., "Overexpression of interleukin-2 by a recombinant herpes simplex virus type 1 attenuates pathogenicity and enhances antiviral immunity", *J. Virol.* 76: 9069-9078 (2002).
Heineman et al., "The varicella-zoster virus (VZV) open reading frame 47 (ORF47) protein kinase is dispensable for viral replication and is not required for phosphorylation of ORF63 protein, the VZV homolog of herpes simplex virus ICP22", *J. Virol.* 69:7367-7370 (1995).
Kennedy et al., "Varicella-zoster virus gene expression in latently infected and explanted human ganglia", *J. Virol.* 74: 11893-11898 (2000).
Kennedy et al., "Varicella-zoster virus gene expression in latently infected rat dorsal root ganglia", *Virology* 289:218-223 (2001).
Kenyon et al., "Varicella-zoster virus ORF47 protein serine kinase: characterization of a cloned, biologically active phosphotrasnferase and two viral substrates, ORF62 and ORF63", *J. Virol.* 75:8854-8858 (2001).
Kinchington et al., "The transcriptional regulatory proteins encoded by varicella-zoster virus open reading frames (ORFs) 4 and 63, but not ORF61 are associated with purified virus particles", *J. Virol.* 69:4274-4282 (1995).

(Continued)

*Primary Examiner* — Nicole Kinsey White
(74) *Attorney, Agent, or Firm* — Edwards Wildman Palmer LLP; Peter F. Corless; Christopher R. Cowles

(57) ABSTRACT

Viruses having weakened ability to establish and/or maintain latency and their use as live vaccines are described. The vaccines have one or more alterations in genes that provide continued virus replication but that inhibit latency. The vaccine materials and methods for their construction are exemplified with the varicella zoster virus. Deletion of a significant portion from both copies of the varicella zoster gene ORF63 was shown to inhibit establishment of a latent infection from a live vaccine form of the virus. Insertion of an additional ORF62 gene which is partially truncated with the ORF63 deletion inhibited establishment of latency and allowed normal growth of the virus. Other desirable viral antigen encoding sequence(s) and/or cytokine genes advantageously may replace deleted genetic material to enhance a desired immunological response. Aspects of the discovery pertain to live vaccines of other viruses, and can provide a variety of vaccines having greater safety.

7 Claims, 5 Drawing Sheets

(56) References Cited

OTHER PUBLICATIONS

Leib et al., "Immediate-Early Regulatory Gene Mutants Define Different Stages in the Establishment and Reactivation of Herpes Simplex Virus Latency", *Journal of Virology* 63(2):759-768 (1989).

Leong et al., "Selective induction of immune responses by cytokines coexpressed in recombinant fowlpox virus", *J. Virol.* 68: 8125-8130 (1994).

Lungu et al., "Aberrant intracellular localization of varicella-zoster virus regulatory proteins during latency", *Proc. Natl. Acad. Sci. USA* 95:7080-7085 (1998).

Mahalingam et al., "Expression of protein encoded by varicella-zoster virus open reading frame 63 in latently infected human ganglionic neurons", *Proc. Natl. Acad. Sci. USA* 93:2122-2124 (1996).

Ng et al., "Phosphorylation of varicella-zoster virus open reading frame (ORF) 62 regulatory product by viral ORF 47-associated protein kinase", *J. Virol.* 68:1350-1359 (1994).

Parcells et al., "Characterization of Marek's disease virus insertion and deletion mutants that lack US I (ICP22 homolog), US 10, and/or US2 and neighboring short component open reading frames", *J. Virol.* 68: 8239-8253 (1994).

Ramsay et al., "Enhancement of mucosal IgA responses by interleukins 5 and 6 encoded in recombinant vaccine vectors", *Reprod. Fertil. Dev.* 6:389-392 (1994).

Rentier et al., "Lessons to be learned from varicella-zoster virus", *Veterinary Microbiology* 53(1-2):55-66 (1996).

Sadzot-Delvaux et al., "Varicella-zoter virus latency in the adult rat is a useful model for human latent infection", *Neurology* 45(Suppl8):S18-S20 (1995).

Sato et al., "Varicella-zoster virus ORF47 protein kinase, which is required for replication in human T cells, and ORF66 protein kinase, which is expressed during latency, are dispensable for establishment of latency", *Journal of Virology* 77(20):11180-11185 (2003).

Sato et al., "Varicella-zoster virus (VZV) ORF17 protein induces RNA cleavage and is critical for replication of VZV at 37° C., but not 33° C.", *J. Virol.* 76:11012-11023 (2002).

Sharrar et al., "The postmarketing safety profile of varicella vaccine", *Vaccine* 19(7-8):916-23 (2000).

Sommers et al., "Mutational analysis of the repeated open reading frames, ORFs63 and 70 and ORFs64 and 69", *J. Virol.* 75:8224-8239 (2001).

Stevenson et al., "Phosphorylation and nuclear localization of the varicella-zoster virus gene 63 protein", *J. Virol.* 70:658-662 (1996).

Wise et al., "Postlicensure safety surveillance for varicella vaccine", *JAMA* 284(10):1271-1279 (2000).

Xia et al., "Varicella-zoster virus ORF21, which is expressed during latency, is essential for virus replication but dispensable for establishment of latency", *J. Virol.* 77(2):1211-1218 (2003).

A.P.N. Ambagala et al., "A varicella-zoster virus mutant impaired for latency in rodents, but not impaired for replication in cell culture", Virology, vol. 399, pp. 194-200 (2010).

J.I. Cohen et al., "Absence or Overexpression of the Varicella-Zoster Virus (VZV) ORF29 Latency-Associated Protein Impairs Late Gene Expression and Reduces VZV Latency in a Rodent Model", Journal of Virology, pp. 1586-1591 (2007).

J.I. Cohen et al., "Rodent Models of Varicella-Zoster Virus Neurotropism", Curr Top Microbiol Immunol. Mar 12. [Epub ahead of print], (2010).

J.I. Cohen et al., "Strategies for Herpes Zoster Vaccination of Immunocompromised Patients", JID 2008:197 (Suppl 2), pp. S237-S241 (2008).

Baiker et al., "The Immediate-Early 63 Protein of Varicella-Zoster Virus: Analysis of Functional Domains Required for Replication In Vitro and for T-Cell and Skin Tropism in the SCIDhu Model In Vivo", *J Virol.* 8(3):1181-1194 (2004).

Bontems et al., "Phosphorylation of varicella-zoster virus IE63 protein by casein kinase influences its cellular localization and gene regulation activity," *J. Bio. Chem.* 277:21050-21060 (2002).

Brunell et al., "Viral gene expression in rat trigeminal ganglia following neonatal infection with varicella-zoster virus", *J. Med. Virol.* 58:286-290 (1999).

Cohen et al., "The varicella-zoster virus open reading frame 63 latency-associated protein is critical for establishment of latency", *Journal of Virology* 78(21):11833-11840 (2004).

Cohen et al., "Generation of varicella-zoster virus (VZV) and viral mutants from cosmid DNAs: VZV thymidylate synthetase is not essential for replication in vitro", *Proc. Natl. Acad. Sci. USA* 90:7376-7380 (1993).

Cohrs et al., "Analysis of individual human trigeminal ganglia for latent herpes simplex virus type 1 and varicella-zoster virus nucleic acids using real time PCR", *J. Virol.* 74:11464-11471 (2000).

Davison et al. "The complete DNA sequence of varicella-zoster virus", *J. Gen. Virol.* 67:1759-1816 (1986).

\* cited by examiner

Figure 2

1.  1 HPEYGSAPSPEDVR--LERGPGAFCAPPWRPDVARLSEDTNKLFRCIATSSLNVTPDSRA 58
    59 LRRALLDFYMMGRTGQRPTRACWETLLQLSPEQSRPLRRTLREVNRRSPHDRSFLYPPPD 118
    119 IPPPLFALECDVS 131

2.  26 KMEYGSAPGPLNGRd-TSRGPGAFCTPGWEIHPARLVEDINRVFLCIAQSSGRVTRDSRR 84
    85 LRRICLDFYLMGRTRQRPTLACWEELLQLQPTQTQCLRATLMEVSHRPPRGEDGFIEAPN 144
    145 VPLHRSALECDVS 157

3.  104 HPEYGSVVASRDLRayLTHGPGAFCSPPWRCDLKRLMKDVNIMFRCIATSSVNVSSDSRA 163
    164 LRRALLDFYIMGYTNQRPTRACWETLLQLSSEQARPLRATLRHLNTTEPCDRRFLEPPTQ 223
    224 VPPILFGQECDVS 236

4.  32 HPEYGSDSSDQDFE--LNN-VGKFCPLPWKPDVARLCADTNKLFRCFIRCRLNSGPFHDA 88
    89 LRRALFDIHMIGRMGYRLKQAEWETIMNLTPRQSLHLRRTLRDADSRSAHPISDIYASDS 148
    149 IFHPIAASSGTIS 161

5.  29 HDEYGQISLGSPVE--SSNSTGNFCAPPWMPDIPRLSNDTCKIFRCLTSCRLNCAPFHDA 86
    87 LRRALLDMHMLGRMGFRLRQHEWERIMQLTPDESINLRRTLLEADERSSHCMPNVYASD- 145
    146 ISNSLEAGTMQVT 158

6.  32 NEDCDENVTIDGIG---EEYAQFFMSPQWVPNLHRLSEDTKKVYRCMVSNRLNYFPYYEA 88
    89 FRRSLFDMYMLGRLGRRLKRSDWETIMHLSPTQSRRLHRTLRFVERRIIPSNSYIRTSGH 148
    149 VPPSRALPTDTNL 161

7.  22 RVVSGPAPADEHAR----RGPGAFCPEDWRPEALRLAIDVNTLFRCIATGSAFVTADTRA 77
    78 LRRALVGFFLLGYTGATPTDACWEALLQLSPEQAGPLRRLLRAAAAAGPRARP-LSPPAR 136
    137 LPGPLFGAECDVS 149

8.  63 HPEYGMPLSPRALRpyLARGPGAFCAPPWRPDVNRLAGDVNRLFRGISTSSIHVTEDSRT 122
    123 LRRALLDFYAMGYTHTRPTLECWQSLLQLLPEQSFPLRATLRALNSEDRYEQRFLEPPSD 182
    183 PPNTLFGEECDVS 195

9.  55 HPEYGPPPDPEEVRvhGARGPGAFCAAPWRPDTRRLGADVNRLFRGIAVSAADVTGDTRA 114
    115 LRRALFDFYAMGYTRQRPSAPCWQALLQLSPEQSAPLRSALRELNERDVYDPR-VLSPPV 173
    174 IEGPLFGEECDVD 186

10. 25 AREYGSVTPGLHSNd-LEHGPGAFCAPPWSLDVARLVKDINRMFLCIARASGRVTRDSRT 83
    84 LRRICVDFYLMGRLKQRPTVTCWEELLQLQPTQTRCLRATLADVARRSPITEE-FIDPPD 142
    143 IPLHRIALECDVS 155

11. CTAGTTGGCCGCGGCGGCCTCCC

12. GGGAGGCCGCCGCGGCCAA

13. AATTGTAGGCCGCCGCGGCCA

14. AGCTTGGCCGCGGCGGCCTAC

15. CCGGAGAGCCTAGGAGACT

16. CCGGAGTCTCCTAGGCTCT

Actual Structure of VZV ROka63NLS

1 2 3 4 5 6 7 8 9 9A 10 11 12 13 14 15 16 17 18 19 20 21 22 23 24 25 26 27 28 UL 29 30 31 32 33 34 35 36 37 38 39 40 41 42 43 44 45 46 47 48 49 50 51 52 53 UL 54 55 56 57 58 59 60 61 62 63 Δ 64 | IR | 65 66 67 68 | US | 64 63 Δ 62 | IR |

(homologous) 62 63 Δ 64

64 62 Δ (non-homologous)

SAFER ATTENUATED VARICELLA-ZOSTER VIRUS VACCINES WITH MISSING OR DIMINISHED LATENCY OF INFECTION

CROSS REFERENCE TO RELATED APPLICATION

This application is a 371national stage application of PCT/US05/021788, filed Jun.22, 2005, which application claims priority to provisional application Serial No. 60/583,399, filed Jun. 29, 2004, the contents of which are incorporated herein in their entirety.

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

FIELD

This disclosure relates to recombinant vaccines, and more particularly relates to live vaccines.

BACKGROUND

Chickenpox is caused by acute infection with varicella-zoster virus (VZV). The virus spreads throughout the body and enters cells of the nervous system. Latent infection occurs and the virus establishes itself in dorsal root and cranial nerve ganglia. The latent virus subsequently can reactivate and present as zoster (shingles). Researchers and pharmaceutical companies have developed chickenpox vaccines but the side effect of shingles due to the live virus establishing a latent infection is still of concern. The ability of a live virus vaccine to enter and maintain a latent infection phase therefore can compromise the safety of live viral vaccines. Any change to the virus that decreases the probability of establishing or maintaining a latent infection can bring significant public health benefits.

Live vaccines are very popular despite the possibility of latent infection. For example, the live attenuated VZV vaccine based on the "Oka virus" (see, U.S. Pat. No. 3,985,615) prevents chickenpox but the virus used in this vaccine can enter a latent infection phase in vaccinated individuals and later cause zoster (Sharrar et al., Wise et al.). The Oka virus is attenuated. However the reason for this attenuation and its significance to the latency problem is unknown. Improved vaccines both for humans and for veterinary care, are needed that comprise altered viruses that present less risk of establishing or maintaining a latent infection and therefore less likely to reactivate.

Recombinant DNA technology can be used to alter viruses. For example, as shown in FIG. 1, the VZV genome is 124,884 bp in length (line 1) and contains unique long (UL), unique short (US), internal repeat (IR) and terminal repeat (TR) regions (line 2). Of the VZV genes, ORF63 and ORF70 encode the same ORF63 protein sequence. According to several reports, the ORF63 genes are active during latency of VZV (Mahalingham et al 1996; Lungu et al 1998; Debrus et al 1995; Cohrs et al 2000; Kennedy et al 2000; Kennedy et al 2001; Sadzot-Delvaux 1995). However, Sommer et al. reported viral "replication required at least one gene copy" and therefore deletion of the ORF63 gene copies would not be helpful for making a live vaccine (J. Virology 75: 17 p. 8224-8239 September 2001). The ORF63 protein is present in virions (Kinchington et al 1995) and is a phosphorylated protein in VZV infected cells (Ng et al 1994). ORF63 protein can be phosphorylated by the VZV ORF47 protein kinase (Kenyon et al 2001) and by casein kinases I and II (Bontems et al 2002; Stevenson et al 1996). However, the VZV ORF47 protein kinase is not required for VZV replication (Heineman et al 1995).

The ORF63 protein contains a nuclear localization signal (Stevenson et al 1996) that may be involved in regular functioning of this protein. ORF63 protein for example localizes to the nucleus in infected cells, and to a lesser extent to the cytoplasm (Debrus et al 1995). In contrast, during latent infection ORF63 protein is located in the cytoplasm (Mahalingham et al 1996); during reactivation the protein moves to the nucleus (Lungu et al 1998). Deletion of the nuclear localization signal or mutations of serine and threonine residues (important for phosphorylation of the protein) in the carboxy half of the protein to alanine residues results in increased localization of the protein to the cytoplasm.

Thus, the search for technical improvements to replication competent vaccines needs new paradigms for selecting genetic weak points and making intelligent changes that can alleviate the latent infection problem.

SUMMARY OF THE DISCLOSURE

Discoveries were made that alleviate the shortcomings reviewed above. One embodiment relates to a virus that has been modified so as to impair its ability to establish latency. One embodiment provides an attenuated live virus vaccine for an animal such as a mammal, the vaccine having impaired ability to establish latency; comprising a recombinant virus that substantially lacks a phosphoprotein gene that is not required for growth of the virus in cultured cells but is important for establishing a latent infection in the mammal. In embodiments, the gene is homologous to the varicella zoster virus and is found in simian varicella virus, feline herpes 1, equine herpes 1, equine herpes 4, pseudorabies virus, canine herpes 1, bovine herpes 1, Marek's disease virus (of chickens), Laryngotracheitis virus, Meleagrid herpes virus 1, or herpes simplex virus. Each such gene can be identified as having sequence similarity to the ORF63 sequence of varicella zoster virus and are particularly contemplated for embodiments. In an embodiment, a gene that encodes a protein sequence portion with sequence homology to the conserved region of the ORF gene product of varicella zoster virus is substantially removed or modified to make a live vaccine of lesser latency. Desirably, the protein sequence encoded by the viral gene is at least 10%, 25%, 27%, 28%, 40%, 45%, 50% or at least 56% identical to the conserved region of the ORF63 gene product. In another embodiment, a live vaccine of a virus that infects nervous systems, but which is not listed here, is constructed by altering a gene of the virus that has a region that is at least 10% identical in amino acid sequence to a varicella zoster virus gene, such as the ORF63 gene.

Another embodiment provides an attenuated live virus vaccine for a mammal, the vaccine having impaired ability to establish latency; comprising a recombinant virus that substantially lacks a gene for a protein encoded by an mRNA, wherein the mRNA is transcribed during normal latency. Yet another embodiment provides an attenuated live virus vaccine for an animal such as a mammal, the vaccine having impaired ability to establish latency, comprising a recombinant virus that substantially lacks a protein encoding a gene, the gene being encoded by a nucleic acid sequence that is complementary to a nucleic acid and is homologous to the ORF63 gene of varicella-zoster virus.

A further embodiment provides an attenuated live virus vaccine that has impaired ability to establish latency, wherein the virus is selected from the group consisting of herpes simplex virus, varicella-zoster virus, Marek's disease virus and pseudorabies virus. Yet a further embodiment provides an attenuated live virus vaccine against a target virus that has impaired ability to establish latency, comprising a varicella-zoster virus missing substantial parts of the ORF63 genes and substituted therefore with at least one gene that encodes at least one protein epitope of the target virus.

Another embodiment provides a live virus vaccine, having impaired ability to establish latency, comprising a recombinant virus that has at least one intact ORF62 gene but that substantially lacks a nucleic acid sequence that is complementary to a nucleic acid that hybridizes with the ORF62 gene of varicella-zoster virus. Desirably, the nucleic acid sequence includes at least a portion of the amino terminal protein sequence encoding the end of the ORF62 region. This region may correspond to, for example, the upstream sequence only, or the upstream sequence plus coding region of 0-10 amino acids, 10-25 amino acids, 20-40 amino acids, 30-50 amino acids, 40-60 amino acids, 50-70 amino acids, 75-100 amino acids or more.

According to an embodiment, an amino terminal portion of the ORF62 protein is coded for and expressed. Expression leads to the translation into a partial protein, which then alters regulation of the viral genome, in a manner that allows replication to wild type titers despite inhibition of latency. The inhibition of latency may arise, for example, by an alteration to ORF63 gene sequence(s), to alteration of one or more ORF62 gene sequences, or both. In an embodiment, replication of a virus is enhanced without increasing latency by addition of the partial ORF62 gene sequence to the virus.

Another embodiment provides a vaccine, wherein the recombinant virus further substantially lacks a gene selected from the group consisting of the ORF63 gene of varicella-zoster virus, the ORF 70 gene of varicella-zoster virus, the ICP22 gene of the herpes simplex virus, the US1 gene of the Marek's disease virus, and the ICP22 homologue gene of the pseudorabies virus. Yet another embodiment provides a vaccine, wherein the recombinant virus is impaired for latency but replicates to wild-type titers in vitro. Another embodiment provides a live virus vaccine, the vaccine having impaired ability to establish latency, and comprising a recombinant virus that has at least one intact ORF62 gene but that substantially lacks a nucleic acid sequence that is complementary to a nucleic acid that hybridizes with the ORF62 gene of varicella-zoster virus. In yet another embodiment, the vaccine comprises a recombinant virus that further substantially lacks a gene selected from the group consisting of the ORF63 gene of varicella-zoster virus, the ORF 70 gene of varicella-zoster virus, the ICP22 gene of the herpes simplex virus, the US1 gene of the Marek's disease virus, and the ICP22 homologue gene of the pseudorabies virus.

Another embodiment provides a vaccine, wherein the recombinant virus has an additional partial copy of a gene selected from the group consisting of the ORF62 gene (for a mutant involving the varicella-zoster virus), the ICP4 gene which is the homolog of VZV ORF62 (for a mutant involving the herpes simplex virus), the ICP4 gene of the Marek's disease virus (for a mutant involving the Marek's disease virus), and the ICP4 gene of pseudorabies virus (for a mutant involving the pseudorabies virus).

Another embodiment provides a vaccine, wherein the recombinant virus further substantially lacks the ORF63 gene of the varicella-zoster virus and also has an additional partial copy of the ORF62 gene. A recombinant herpes simplex virus would substantially lack the IPC22 gene and also have an additional partial copy of the ICP4 gene. A recombinant Marek's disease virus or pseudorabies virus would substantially lack the ICP22 gene homologs and also have a partial copy of the ICP4 gene homologs.

Another embodiment provides a method for making an attenuated live virus vaccine targeted against a virus and having impaired ability to establish latency, comprising selecting a virus having one or more copies of a dominant latent phase transcribed gene, altering or removing a substantial part of each copy of the latent phase transcribed gene to form an attenuated virus having impaired ability to establish latency, and culturing the attenuated virus to an amount suitable for a vaccine. Desirably, the latent gene has a region that is at least 10%, 25%, 27%, 28%, 40%, 45%, 50% or at least 56% identical to the conserved region of the ORF63 gene product. The gene may be selected on this basis. Yet another embodiment provides a method for making an attenuated live virus vaccine targeted against a virus and having impaired ability to establish latency, comprising selecting a virus having one or more copies of a dominant latent phase transcribed gene, altering or removing a substantial part of each copy of the latent phase transcribed gene to form an attenuated virus having impaired ability to establish latency, and culturing the attenuated virus to an amount suitable for a vaccine. In a desirable embodiment this method selects "one or more copies of an immediate-early gene" by determining which gene of the virus has homology to the ORF63 gene of varicella zoster virus. Other embodiments will be appreciated from a reading of the specification.

BRIEF DESCRIPTION OF THE DRAWINGS

FIG. 2 shows the conserved regions of varicella zoster virus ORF63and nine other viruses (SEQ ID NOs: 1-10, as numbered, in order of appearance) and their comparison with a consensus sequence. Nucleotide sequences, described in detail below, are also shown (SEQ ID NOs: 11-16, as numbered, in order of appearance).

FIG. 3 depicts the structure of a new VZV mutant, ROka63NLS, which has both a 21 aa deletion in the nuclear localization signal (NLS) of ORF63 and an unexpected rearrangement of its genome. The virus is impaired for latency in rodents and grows to wild-type titers in cell culture.

FIG. 4 is a growth curb that shows that ROka63NLS is not impaired for growth in vitro.

DETAILED DESCRIPTION OF THE DISCLOSURE

Figure 1:
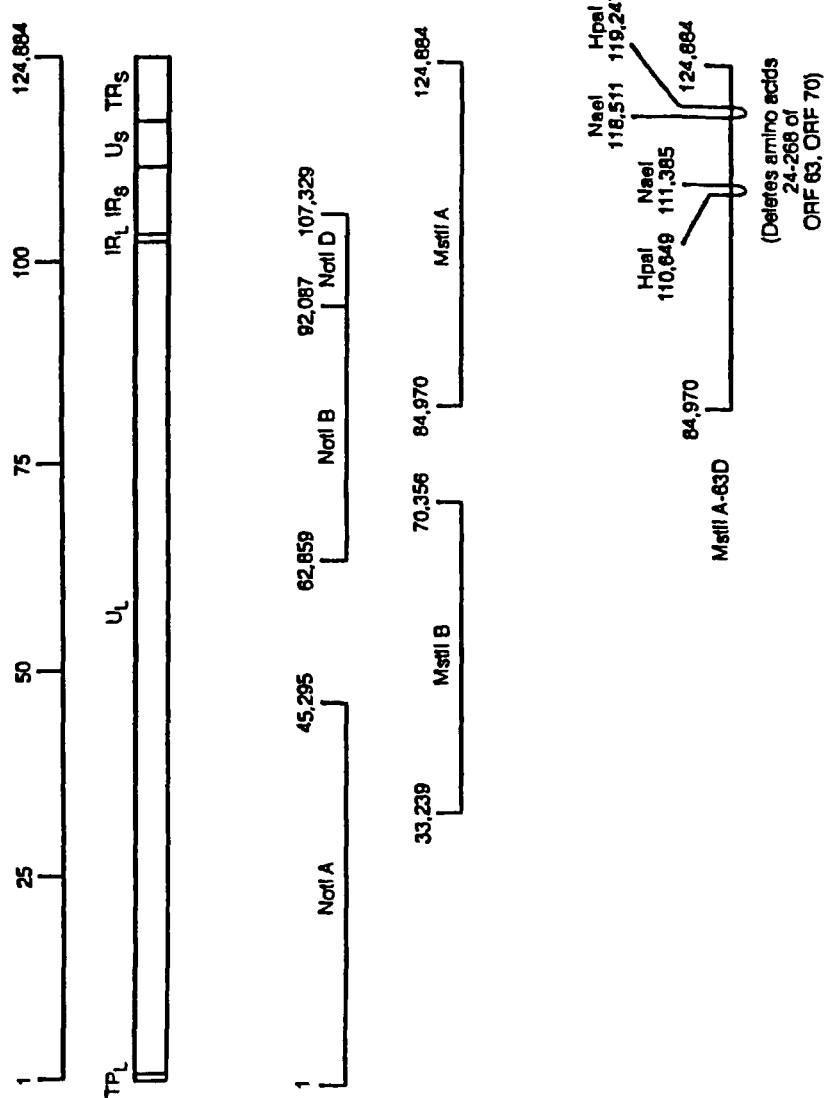
FIG. 1 depicts the construction of recombinant VZV with a deletion in ORF63. The four cosmids used to produce infectious virus span the VZV genome (lines 3 and 4). Cosmid MstII63D (line 5) is deleted in ORF63, as shown.

It was discovered that modification, particularly by deletion, of a gene encoding a protein such as a phosphorylated protein found in the cytoplasm during latency of a virus creates an altered virus that can replicate in vitro but has markedly diminished ability to establish a latent infection. Moreover, live vaccines that contain such modified virus should be safer than regular unmodified live virus vaccines. In one embodiment, substantially all (at least 30%, 40%, 50%, 75%, 85%, 90% or more and particularly at least 50%) of the protein coding sequence of all copies of the gene used in the virus or virus vaccine is deleted. In a desirable embodiment, the gene is selected by examination of homology with a conserved region of a varicella zoster virus ORF62 gene product. In another embodiment, the gene is selected by examination of homology with a conserved region of a varicella zoster virus ORF63 gene product.

Advantageously, the region is at least 10%, 25%, 27%, 28%, 40%, 45%, 50% or at least 56% identical to the conserved region of the compared gene product. Moreover, particularly in the case of selection of an ORF62 homology, a desirable gene advantageously contains a deletion on the carboxyl terminal (encoded protein) side of the gene. In this preferred case, the percent homology is calculated without reference to the deleted sequence. The gene may be selected or designed on this basis.

In a desirable embodiment, a VZV or HSV is made having at least one full length and one altered form of ORF62 or ICP4 (a homolog of the ORF62 gene product). The altered form desirably misses at least 1%, 2%, 3%, 4%, 5%, 6%, 8%, 10%, 12%, 15%, 20%, 25%, 30%, 35%, 40% or more of the carboxyl terminal end, although other alterations can be carried out that will have at least some beneficial effect on the protein. In an embodiment, the virus additionally has a ICP22 gene deletion. A live vaccine can be made from the altered virus and is particularly contemplated. In another embodiment, a section of a gene homologous to the ORF62 and/or ORF63 gene products and that encodes a nuclear localizing region is substantially missing. In another embodiment, a KRRR nuclear localizing sequence is missing. In yet another embodiment, the gene is modified such that phosphorylation of the protein is reduced and the protein has less tendency to enter the nucleus. In yet another embodiment, one or more serines and/or theonines that become phosphorylated are altered to another amino acid that cannot become phosphorylated. In yet another embodiment, two or more of these features are combined. In yet another embodiment, the gene is mutated to decrease the ability of the final protein product from entering the nucleus.

In a desirable embodiment an ORF62 gene of 1310 amino acid coding region or a similar sized homologous protein is truncated to remove 0-10%, 10-25%, 25-35%, 35-50%, 50-65% or more of the carboxyl terminal side of the protein. One embodiment that was found to work well was the truncation of a 1310 amino acid coding region to an 840 amino acid coding region. In another embodiment the remaining amino terminal side region is between 700-840 amino acids, 600-700 amino acids, 500-600 amino acids, or even less.

In yet another embodiment, the viral kinase from ORF47, as described by Kenyon et al. is modified or substantially deleted to remove its kinase activity. In yet another embodiment, both the ORF47 kinase gene and the ORF63 genes are modified. In another embodiment where an ORF63 gene homologue from another virus is substantially deleted or modified, a viral kinase in that other virus also is modified or substantially deleted to remove its kinase activity.

In another embodiment, a vaccine is prepared from one or more of the viruses described herein, by combining one or more adjuvants with the virus or viruses in a form suitable for administration. In another embodiment, a vaccine is prepared from one or more of the viruses described herein, by combining one or more excipients with the virus or viruses in a form suitable for oral delivery. In another embodiment, a vaccine is prepared from one or more of the viruses described herein by forming a sterile suspension of the virus or viruses suitable for administration. In an embodiment, the vaccine is prepared in a form suitable for injection.

It was discovered using the varicella zoster virus genome as a model system that, contrary to knowledge in the field, a gene that encodes a phosphorylated protein, or other homologous protein as described herein, is important for establishing a latent infection (i.e. absence of the gene lowers the frequency of latent infection by at least 50%, and more preferably by at least 75%, 85%, 90%, 95%, 98%, 99% or by even 100%) but is not required for replication in vitro. In a desirable embodiment, each copy of such gene is partly, mostly, or all deleted. In another embodiment, the gene cop(ies) are modified by mutation. In many embodiments one or more copies of a gene are modified (by deletion, mutation or both) the same way and for brevity the ORF63 gene is mentioned by name. That is, the term "ORF63 gene" means both ORF63 and ORF70. A virus having a deletion of the ORF63 gene preferably has the same deletions in both the ORF63 and ORF70 gene copies. A deletion generally leads to ineffective or altered protein. In the case of the ORF63 and ORF70 genes an exact correspondence between both genes ORF63 and ORF70 is desired in many embodiments. In the case of ORF62 gene modification, it was surprisingly found that addition of a modified form (removal of carboxyl terminal end) can provide normal replication while preserving latency. Live virus vaccines having impaired propensity to develop a latent infection can be made from a variety of viruses, genes and gene modifications as described herein. Desirable methods for making a virus are described next. Changes to a varicella zoster virus strain are used to exemplify the invention for the chickenpox vaccine.

Gene Selection

A variety of genes are expressed during the latency period of a viral infection. It was discovered during study of the varicella zoster system that a gene that is transcribed with high efficiency and in many studies is the most abundantly transcribed gene (compared to other genes) during viral latency has particularly useful properties in embodiments of the invention. For a given virus or virus strain, such a gene may be selected using a routine procedure such as the measurement of viral mRNA during latency to determine which viral mRNA is abundant or most abundant.

In yet another embodiment, a gene is selected that has negative transcription regulatory activity. Methods for determining regulatory activity are known. For example, Bontems et al. describes negative transcription regulatory activity found for the ORF63 gene. In another embodiment, a gene that is not required for growth or replication but which is involved in latency is selected for modification. The gene may be determined by preparing mutants such as premature termination or deletion mutants and determining their effects on replication (e.g. synthesis of viral gene(s) or propagation of virus).

In an embodiment of the invention, a gene is chosen having a nucleic acid sequence that shares at least 25% homology with the varicella-zoster ORF63 or ORF62 gene. In another embodiment, the chosen gene shares at least 50%, 66%, 75%, 80%, 85%, 90%, 95% or more homology with the varicella-zoster ORF63 or ORF62 gene. Percent homology is determined by placing the protein coding sequence of the "test" gene to be compared in a best fit alignment next to the protein coding portion of the ORF63 or ORF62 gene. The total number of identical nucleic acids that line up is divided by the total number of nucleic acids of the test gene protein coding region. Homology is evaluated by computer using any of a variety of sequence comparison programs known in the art. Examples of such programs include, but are by no means limited to, TBLASTN, BLASTP, FASTA, TFASTA, and CLUSTALW as reviewed in U.S. Pat. No. 6,472,517. In a particularly preferred embodiment, protein and nucleic acid sequence homologies are evaluated using the Basic Local Alignment Search Tool ("BLAST") which is well known in the art.

One or more copies of a gene may be a) mutated or otherwise altered and/or b) added to an existing viral genome. For example, a gene fragment comprising the coding region and upstream sequence may be added to an existing viral nucleic acid that contains normal ORF62.

In another embodiment, a gene homologous to the ORF63 gene and/or ORF62 gene is selected from another virus. Homologous genes are known and more are expected to be discovered. For example, the US1 gene of Marek's disease virus as described by Parcells et al., and the analogous gene from the pseudorabies virus as described by Fuchs et al. may be selected for vaccines against those respective viruses. Various genes homologous to ORF62 may be altered as will be appreciated by a skilled artisan. For example, ICP4 of HSV or the corresponding ICP4 protein in pseudorabies virus or Marek's disease virus may be altered, particularly by deletion in the carboxyl terminal side of the protein and inserted into the corresponding virus to make a vaccine against the virus. Of course, genes that are less homologous also may be selected. For example in the case of ORF63, a gene that encodes a protein that becomes phosphorylated may be selected, optionally with a second gene that encodes a viral kinase that acts upon the protein that becomes phosphorylated. Most advantageous in this respect is the selection of a phosphorylated protein that has negative transcription regulatory activity.

Table 1 shows representative genes having suitable amino acid coding homology to the ORF63 gene of varicella zoster virus that may be selected. Table 2 shows representative genes having suitable amino acid coding homology to the ORF62 gene of varicella zoster virus. The definition of homology is well known to a skilled artisan and can be, for example seen by example on the NCBI conserved domain database. See FIG. 2, which illustrates some homology results that compare a consensus sequence (SEQ ID NO: 1) with the varicella zoster virus ORF63 conserved sequence, (SEQ ID NO: 2), feline herpes sequence (SEQ ID NO: 3), Marek's disease virus sequence (SEQ ID NO: 4), Laryngotracheitis virus sequence (SEQ ID NO: 5), Meleagrid herpes virus 1 sequence (SEQ ID NO: 6), bovine herpes 1 sequence (SEQ ID NO: 7), equine herpes sequence (SEQ ID NO: 8), pseudorabies virus sequence (SEQ ID NO: 9), and simian varicella virus sequence (SEQ ID NO: 10). Other viruses known and to be discovered, particularly that infect ganglia of the nervous system have or are expected to have analogous genes that expressly are intended as embodiments of the invention. Desirably, a viral genome is compared with the consensus sequence such as that exemplified for ORF63 and shown in FIG. 2 (or a related sequence) and a homology fit of typically at least 10% identity, when found, indicates the presence of a gene that is analogous to an ORF63 gene (or an ORF62 gene) as described herein.

TABLE 1

VZV ORF63 Protein Homologies with Herpesviruses

| Virus | Animal | Identical Amino Acids | Conserved Amino Acids |
|---|---|---|---|
| Simian varicella virus | Rhesus | 77/134 (57%) | 95/134 (70%) |
| Feline herpes 1 | Cat | 77/134 (57%) | 95/134 (70%) |
| Equine herpes 1 | Horse | 54/120 (45%) | 63/120 (52%) |

TABLE 1-continued

VZV ORF63 Protein Homologies with Herpesviruses

| Virus | Animal | Identical Amino Acids | Conserved Amino Acids |
|---|---|---|---|
| Equine herpes 4 | Horse | 53/120 (44%) | 65/120 (54%) |
| Pseudorabies virus | Pig | 46/105 (43%) | 56/105 (53%) |
| Canine herpes 1 | Dog | 41/96 (42%) | 54/96 (56%) |
| Bovine herpes 1 | Cow | 37/78 (47%) | 44/78 (56%) |
| Marek's disease virus | Chicken | 26/92 (28%) | 35/92 (38%) |
| Laryngotracheitis virus | Bird | 25/86 (29%) | 33/86 (38%) |
| Meleagrid herpesvirus 1 | Turkey | 22/84 (26%) | 32/84 (38%) |
| Herpes simplex 1 | Human | 30/85 (35%) | 38/85 (44%) |
| Herpes simplex 2 | Human | (similar to HSV-1) | |

TABLE 2

VZV ORF62 Protein Homologies with Herpesviruses

| Virus | Animal | Identical Amino Acids | Conserved Amino Acids |
|---|---|---|---|
| Simian varicella virus | Rhesus | 598/1313 (45%) | 717/1313 (54%) |
| Feline herpes 1 | Cat | 224/453 (49%) | 261/453 (57%) |
| Equine herpes 1 | Horse | 236/469 (50%) | 271/469 (57%) |
| Equine herpes 4 | Horse | 235/466 (50%) | 270/466 (57%) |
| Pseudorabies virus | Pig | 211/388 (54%) | 238/388 (61%) |
| Canine herpes 1 | Dog | 208/430 (48%) | 255/430 (59%) |
| Bovine herpes 1 | Cow | 211/369 (57%) | 233/369 (63%) |
| Marek's disease virus | Chicken | 124/394 (31%) | 168/394 (42%) |
| Laryngotracheitis virus | Bird | 37/135 (27%) | 54/135 (40%) |
| Meleagrid herpesvirus 1 | Turkey | 135/377 (35%) | 174/377 (46%) |
| Herpes simplex 1 | Human | 201/395 (50%) | 229/395 (57%) |
| Herpes simplex 2 | Human | 223/493 (45%) | 254/493 (51%) |
| Herpes B virus | Rhesus | 198/370 (53%) | 224/370 (60%) |

A gene also may be selected by virtue of its dual functions during maintenance of latency and during replication. A gene that is needed for replication and has a role in replication but that also has another function during latency is particularly desirable. Also desirable is a gene whose protein product is found mostly in the nucleus during replication but found mostly in the cytoplasm during latency.

A given gene's effect on establishing or maintaining latency may be determined by infecting animals with virus that does not express the gene and determining the amount of viral DNA in the animal at least one month after the infection.

In a related embodiment a gene that is required for growth or replication is mutated to allow growth or replication while interfering with the establishment or continuance of latency. In practice, a large number of mutations may be made to a gene that is suspected to have a strong effect on latency (by virtue of its transcription during latency) followed by a screening assay to select for normal or altered (slower) growth or replication. Altered genes can be further selected for effects on latency.

A latency assay may be used to determine the effect on latency as is known to a skilled artisan. In yet another embodiment, a gene that encodes a tegument protein is selected. In yet another embodiment, a gene that generates the most abundant transcripts during latency is selected. In yet another embodiment, a gene that encodes a viral protein that becomes phosphorylated and which generates high levels of transcripts during latency is selected. In each case, the cited gene parameters may be determined by assay of, for example, gene activity by measuring transcribed RNA in the nucleus, measuring mRNA in the cytoplasm, measuring synthesized protein in the cytoplasm, and/or by information from literature reports. The field of molecular virology has advanced to the level where such assays involve only routine experimentation.

In the varicella zoster virus example, a desirable gene is ORF63 (both ORF63 and ORF70, the term "ORF63" means both copies of this gene and is used for convenience). In another embodiment, the viral kinase that phosphorylates this gene and which is not essential for replication, VZV ORF47 (or a gene with at least 10% homology or more to ORF47) is selected. In an advantageous embodiment both ORF63 and ORF47 are selected for modification.

Another suitable gene is a gene that has negative transcriptional activity, i.e. that represses gene expression. Such a gene in particular is a preferred candidate to mutate for a vaccine. By way of example, gene ORF63 is expressed in latency, and can turn off other viral genes and may allow latency with limited virus gene expression. It was found experimentally that deletion of this gene reduced the ability of the virus to go latent. Likewise, other genes associated with negative transcriptional activity, either known or to be discovered in the future are good candidates for selection.

Another suitable gene is a gene that has positive transcriptional activity, i.e. that activates gene expression. Such a gene in particular is a preferred candidate to truncate and insert into a vaccine. By way of example, gene ORF62 is expressed in latency. While ORF62 turns on other viral genes during virus replication, a truncated form of the protein may interfere with the activity of the wild-type protein, and may turn off other viral genes. It was found experimentally that insertion of a truncated form of the ORF62 gene reduced the ability of the virus to go latent. Likewise, other genes associated with positive transcriptional activity, either known or to be discovered in the future may be used for selection.

A suitable gene also may be selected by determining which viral gene encodes a protein that becomes phosphorylated and/or that is transcribed during latency. In another embodiment, the gene is a viral kinase that phosphorylates a viral protein and that may affect the subcellular distribution of the viral protein. In yet another embodiment, the gene encodes a protein that specifically binds a molecule on or in a particular host cell that the virus inhabits. The term "specifically binds" in this context means that the protein binds to a molecule that is at least ten times more available or present in the host cell compared to a non-host cell, or has at least ten times higher binding affinity to its binding partner in or on the host cell compared with a non host cell. In other embodiments combinations of these conditions are used to select a desirable viral gene.

A variety of other strategies can be used to select a viral gene. A virus that preferentially infects a particular cell type or group in a latent manner often has at least one such gene that has evolved for that particular cell type or group. By modifying the gene(s) as described here, viral replication in vitro may still occur but the virus will have no or diminished ability to establish or maintain latency. Thus, embodiments of the invention, which flow from this understanding include other viruses and genes besides the varicella zoster virus and the ORF63 gene, as will be appreciated by a skilled reader.

Gene Modification

The selected viral gene is modified to remove or inhibit its natural effect in establishing or maintaining latency. For example, one or more base pairs are deleted or otherwise modified and the resulting virus used in formulating a live vaccine having less tendency to establish or maintain a latent infection. In one embodiment the gene lacks a transactivating function for regulating viral infection but is necessary for interacting with the host cell. Accordingly, by removing the activity of this gene, latency can be affected specifically.

Any modification that affects function of the selected gene is useful for decreasing or eliminating the ability of the virus to establish or maintain latency. Most preferably at least 1, 2, 3, 5, 10, 25, 50, 100, 200, 300, 400, 500 or more base pairs are removed. For the ORF63 gene, advantageously at least a portion of the carboxyl terminal end is removed that contains the RKKK sequence or other sequences that are necessary for proper localization or functioning of the gene product. By removing large blocks of nucleic acid from all copies of the gene in a virus, the modified virus will have less tendency to revert to wild type characteristics. In another desirable embodiment mutation of one or more base pairs is carried out by a regular procedure as is known in the art. For example, PCR-based mutagenesis has been used for mutational analysis of the ORF63 gene, as described by Sommers et al.

In a particularly desirable embodiment relevant to phosphorylated proteins such as ORF63, one, or more preferably multiple amino acids are altered to other amino acids and thereby blocks one or more phosphorylations by a kinase. In an embodiment, one or more serines/threonines are altered to prevent or limit phosphorylation by a serine-threonine dependent kinase. By way of example, for the ORF63 protein, at least one, two, three, four, five, six, seven, eight, nine or ten of the serine and threonine amino acids located at Ser-150, Ser-165, Ser-181, Ser-186, Thr-171, Ser-173, Ser-185, Thr-201, Thr-244 and Ser-224 may be converted to other amino acid(s) such as alanine by alternation of the ORF63 and/or ORF70 nucleic acid sequence(s). In another embodiment, other amino acids not mentioned here but that become phosphorylated are modified.

In yet another embodiment, the conformation of the protein is modified by altering the carboxyl terminus of the protein. For example, ORF63 can be modified to inhibit phosphorylation by mutation of the gene. In yet another embodiment, the conformation of the protein that is involved with intermolecular interaction (for example the portion of ORF63 protein that interacts with ORF62 product of varicella zoster virus, as described by Sommers et al.) is modified to inhibit the interaction and thereby interfere with establishment or maintenance of latency. A skilled artisan can determine which portion of a selected protein is involved with intermolecular activities by routine assays. For example, binding assays can be carried out with normal and with mutated forms to determine which mutations decrease binding and thereby inhibit normal protein functioning.

In another embodiment, the nuclear localization signal (if present) of the selected protein is modified or deleted. For the ORF63 genes, the RKKK portion and surrounding amino acids (at least one, two or more on each side) most desirably are deleted. In another embodiment, one or more amino acids are modified. For example, the highly basic RKKK segment may be converted into a less basic or even an acidic segment by changing one or more amino acids to a neutral or acidic form.

In yet another embodiment, multiple small deletions (of between one and 1000) of bases are made in the selected protein encoding gene that includes different portions of the protein. Such deletions may, for example, encompass regions or amino acids that become phosphorylated. In another embodiment, deletions are combined with individual mutations that serve to eliminate phosphorylation sites. Most preferably a virus "substantially lacks" the selected protein gene which has been "substantially deleted." That is, at least 30%, more preferably 50%, and even more preferably at least 60%, 70%, 80%, 90% or 95% of the protein encoding section of the selected gene is deleted. In practice, any portion that affects gene activity may be deleted and have an effect, according to an embodiment of the invention, although alteration by inserting a truncation of the carboxyl terminal protein encoding portion of the ORF62 gene (or another viral gene that like ORF62 turns on gene expression) is particularly desirable. A "substantial" region of only 8%, 7% or even 5% may be deleted and cause an effect. In practice, however, desirably more than such minimum portion should be deleted.

In a most desirable embodiment one or more deletions are made, which removes a protein activity while, at the same time, providing space for adding one or more protein antigen encoding genetic sequences. In a related embodiment a selected viral gene is at least partly deleted and replaced with sequence(s) that encodes one or more epitopes of another viral protein. A viral protein that is synthesized to a high level and that is packaged into the virus, is particularly desired for this embodiment. For example, enough of a protein that forms a viral capsid (or envelope glycoprotein) may be added in place of the deleted portion in-frame with a promoter and initiation codon to allow expression. A skilled artisan may engineer or select a protein that becomes packaged in the regular capsid (or viral envelope). In a related embodiment a promoter or other regulatory sequence is chosen to allow low enough expression as to avoid formation of unstable virus structures.

In yet another embodiment, a cytokine gene is inserted into the site of deletion of a viral genome or even elsewhere in the genome of a viral deletion mutant to improve the immunogenicity of the virus. Such replacement and the effects on immunogenicity are known and readily carried out. For example, insertion of IL-2 into HSV (Ghiasi et al 2002) enhanced the cellular immune response to this virus. Insertion of IL-6 into fowlpox virus (Leong et al 1994) enhanced the systemic and mucosal antibody responses to this virus, and insertion of IL-5 into vaccinia (Ramsay et al 1994) improved the IgA antibody response to this virus. Other cytokine genes may be used as well. Advantageously one or more cytokine genes replaces one or more deletions of a virus used to make a live virus vaccine.

The term "ORF" means open reading frame. For example, ORF63 refers to the gene ("ORF63 gene"), its transcript ("ORF63 transcript" or "ORF63 RNA"), or the protein encoded thereby ("ORF63 protein") in different contexts as used in this disclosure and understood by those skilled in the art. Because ORF70 encodes the same ORF63 gene, ORF63 is used to mean both copies of the gene as used throughout this specification unless mentioned otherwise. Other terms are used in their regularly understood meaning. The term "vaccine" as used herein refers to any compound, molecule, agent, or combinations thereof that is capable of establishing immune responsiveness in a user or a patient to an antigenic substance, such as a virus or another pathogen or exogenous stimulus. A vaccine typically contains inactivated antigenic substance such as the inactivated pathogen. The terms NotI A, NotI BD, MstII A, and MstII B, as used herein, refer to various cosmids utilized in transfection experiments to produce desired mutations in various embodiments. These constructs can be made from known methods.

Formation of Live Virus Vaccines

A wide variety of vaccines can be prepared that incorporate one or more viruses as described herein. In desirable embodiments a live virus is cultured in cells and harvested to produce a vaccine by combining virus particles with one or more stabilizers in a form that does not extensively denature the virus. A variety of culturing techniques, concentration techniques, stabilizers and vaccine formulations are known and may be adapted to the particular virus type used, as are familiar to the skilled artisan.

Generally, preparation of a stabilized live virus vaccine begins with the culture of the virus in a human diploid cell. The virus culture may be purified, for example, by centrifugation, to obtain a more purified virus fraction. Generally a vaccine stabilizer is then added to the virus fraction, and the mixture diluted. The final desired virus concentration typically will be about 10 to 100,000 PFU (plaque-forming units) and more typically 100 to 10,000 PFU or more of virus content per dose of the stabilized live vaccine. Aliquots of the thus prepared live vaccine may be tested for safety, effectiveness and homogeneity, to confirm eligibility as a vaccine.

An important factor in vaccine formulation is the stabilizer, as vaccine potency may be adversely affected by concentration and storage conditions. Stabilizers often used for live vaccines of viruses such of measles, rubella and mumps generally include one or more saccharides, amino acids, sugar alcohols, gelatin and gelatin derivatives, to stabilize the virus and, in many cases keep the virus from denaturing during a concentration step. In an advantageous embodiment a recombinant virus described herein may by formulated into a vaccine using a stabilizer or other additive that includes native or recombinant serum albumin for this purpose. U.S. Pat. No. 6,210,683 provides representative conditions for this embodiment of the invention. U.S. Pat. Nos. 5,728,386, 6,051,238, 6,039,958 and 6,258,362 also contain details for stabilizers and methods for more gentle treatment of live virus vaccines. Each of these disclosures, and particularly those portions that describe stabilizer compositions and stabilizing methods are specifically incorporated by reference in their entireties.

After preparation with a stabilizer, the vaccine may be, for example, stored as a lyophilized vaccine, a lyophilized mixed vaccine, a liquid vaccine or a liquid mixed vaccine. Methods for forming these are known. Typically, a lyophilized vaccine is prepared by lyophilizing the vaccine in a vial or an ampule having a volume of about 3 to 30 ml, tightly sealing and storing at a temperature of 5 degrees Centigrade or less. The stored preparation vaccine typically is used according to instructions attached thereto, as a product insert or a notice on the vial or other container. In many cases, a lyophilized vaccine is re-constituted by addition of sterile distilled water before use, and the resultant solution is inoculated by hypodermic injection in an amount, for example, of 0.5 ml per dose. In another embodiment, the vaccine is provided orally.

In an embodiment a modified virus prepared as described herein is less stable than the wild type from which the virus is derived and a more gentle stabilizer is used. For example, a modified virus that contains one or more added genes that encode other antigens may have a larger amount of genetic material than usual and may be more sensitive to denaturation. In one related embodiment the free divalent cation concentration of the stabilizer or final vaccine formulation is reduced, for example, by the addition of EDTA to counteract this instability. U.S. Pat. No. 6,039,958 for example provides instructions for lowering the concentration of calcium and magnesium in preparations of live virus vaccines. Other techniques described in the literature that alleviate instability and/or facilitate combinations of multiple viruses in the same formulation may of course be used and are contemplated.

Various embodiments of this disclosure are further described by the following examples, which are illustrative of the embodiments but do not in any manner limit the same. Various molecules, reagents, and instruments referred to in the examples and throughout this disclosure are only representative of the larger intended scope. Equivalent or alternative products as understood by immunologists, virologists, and molecular biologists may be employed to carry out the various embodiments.

EXAMPLES

In the examples, Southern blotting and immunoblotting were carried out as follows. Southern blotting assays were performed by isolating VZV DNA from nucleocapsids, cutting the DNA with BamHI, and fractionating the DNA on 0.8% agarose gels. After transferring DNA to a nylon membrane, each blot was probed with a [$^{32}$P]dCTP-radiolabeled probe that corresponds to the 4.65 kb BamHI J fragment of the VZV genome that contains the ORF63 gene.

Immunoblotting assays were performed by preparing protein lysates of VZV infected cells, fractionating the proteins on polyacrylamide gels, transferring the proteins to membranes, and incubating the blots with rabbit antibody to ORF63 protein (Ng et al J Virol 1994; 68:1350-1359) or mouse monoclonal antibody to glycoprotein E (IgE, Chemicon, Temecula, Calif.). The membranes were then incubated with horseradish peroxidase conjugated anti-rabbit or anti-mouse antibody and imaged using enhanced chemiluminescence (Pierce Chemical Company, Rockfield, Ill.).

Example 1

Construction of cosmids and transfections. Cosmids VZV Not I A, Not I BD, Mst II A, and Mst II B are derived from the Oka vaccine strain and encompass the entire VZV genome. Upon transfection into cells these cosmids produce infectious virus (Cohen and Seidel, 1993). The short internal repeat of the viral genome contains a first ORF63 gene copy and the short terminal repeat of the genome contains the second copy ORF70, as shown in FIG. 1. Both the ORF63 and ORF70 gene copies are located in a Sfi I fragment extending from VZV nucleotides 109,045 to 120,854 (Davison and Scott 1986). To clone the VZV Sfi I fragment, two Sfi I sites were inserted into Bluescript SK+ (pBSSK+) (Strategene, LaJolla, Calif.). The plasmid pBSSK+ was modified to include the first Sfi I site by cutting it with Spe I and Sma I; and, a double-stranded DNA, derived from CTAGTTGGCCGCGGCGGC-CTCCC (SEQ ID NO: 11) and GGGAGGCCGCCGCGGC-CAA (SEQ ID NO: 12), was inserted into the site. This Sfi I site is compatible with the Sfi I site at VZV nucleotide 109,045. A second Sfi I site, compatible with the Sfi I site at VZV nucleotide 120,854, was created by digesting the modified pBSSK+ plasmid with EcoRI and HindIII; and, a double-stranded DNA, derived from AATTGTAGGCCGCCGCG-GCCA (SEQ ID NO: 13) and AGCTTGGCCGCGGCGGC-CTAC (SEQ ID NO: 14), was inserted into this site. The resulting plasmid was cut with Sfi I; and, the Sfi I fragment from cosmid MstII A which contains ORF63 and ORF70 (VZV nucleotides 109,045 to 120,854) was inserted to create plasmid pBSSK+SfiI.

A modified plasmid pBSSK+ was constructed in which the NgoM I and Cla I sites were ablated. First, plasmid pBSSK+ was cut with NgoM I and a double-stranded oligonucleotide, derived from CCGGAGAGCCTAGGAGACT (SEQ ID NO: 15) and CCGGAGTCTCCTAGGCTCT (SEQ ID NO: 16), was inserted into the site. The resulting plasmid, pBSSK+AvrII, contains an Avr II site. Plasmid pBSSK+AvrII was cut with Cla I and Kpn I and a single-stranded oligonucleotide—CGGTAC—was inserted into this site to create plasmid pBSSK+AvrIIdCla.

The ORF63 gene from plasmid pBSSK+SfiI was inserted into plasmid pBSSK+AvrIIdCla. Plasmid pBSSK+SfiI was cut with Spe I—located in pBSSK+ adjacent to the site of the VZV insert—and EcoR I—located at VZV nucleotide 117,034—and the resulting 3.9 kb fragment was inserted into the Spe I and EcoR I sites of pBSSK+AvrIIdCla to create plasmid ES. The ORF70 gene from plasmid pBSSK+SfiI was then inserted into plasmid pBSSK+AvrIIdCla. Plasmid pBSSK+SfiI was cut with Avr II—located at VZV nucleotide 112,853 and Hind III—located in pBSSK+ adjacent to the site of the VZV insert, and the resulting 3.9 kb fragment was inserted into the Avr II and Hind III sites of pBSSK+AvrIIdCla to create plasmid AH.

The ORF63 and ORF70 genes were then deleted from plasmids ES and AH, respectively. Plasmid ES was cut with Hpa I (VZV nucleotide 110,649) and Nae I (VZV nucleotide 111,385) and the large blunt ended fragment was ligated to itself. Similarly, plasmid AH was cut with Hpa I (VZV nucleotide 119,247) and Nae I (VZV nucleotide 118,511) and the large fragment was ligated to itself. Mutated plasmid ES was cut with EcoR I and Spe I; and, the ORF63-deleted fragment was inserted in place of the wild-type EcoR I-Spe I fragment into plasmid pBSSK+SfiI. The mutated plasmid AH was cut with Avr II and Hind III, and the ORF70-deleted fragment was inserted in place of the wild-type Avr II-Hind III fragment of the ORF63 deleted plasmid pBSSK+SfiI. Finally, the ORF63-and-ORF70-deleted plasmid pBSSK+SfiI was cut with Sfi I and inserted in place of the wild-type Sfi I fragment of cosmid MstIIA. The resulting cosmid, termed MstIIA-63D, has identical deletions of ORF63 and ORF70 that result in loss of codons 24 to 268; the remaining codons (269-278) are out of frame. Two independently derived clones of plasmids ES and AH were obtained and subsequent reactions were carried out in parallel. Thus, two cosmids, MstIIA-63DA and MstII63-DB, were independently derived.

Recombinant VZV was produced by transfecting human melanoma (MeWo) cells with a plasmid that expresses VZV ORF62 protein and cosmids VZV NotI A, NotI B, MstII B, and MstII A or MstII A-63D. To rescue the deletion in ORF63, a plasmid containing ORF63 and its promoter was constructed. A 5.6 kb Bcl I fragment of VZV (nucleotides 106,592 to 112,215) was inserted into plasmid pMAL-p2X (New England Biolabs, Beverly, Mass.) between nucleotides 445 and 2,645. The resulting plasmid was cut with BclI and the VZV fragment was gel purified.

Example 2

This example describes the deletion of both copies of the ORF63 gene and construction of a rescued virus in which ORF63 is replaced. Cosmids MstIIA-63DA and MstIIA-63 DB were constructed, as described in Example 1 and used to construct viruses with both gene copies ORF63 and ORF70 substantially deleted. Amino acids 24 to 268 of ORF63 and ORF70 were deleted in MstIIA-63DA and MstIIA-63 DB, as shown in FIG. 1. Melanoma cells were transfected with plasmid pCMV62. Cosmids VZV NotI A, Not I BD, MstII A, and MstII B showed cytopathic effects. Recombinant Oka VZV (ROka) was produced following transfection. Transfection of cells with plasmid pCMV62 and cosmids VZV NotI A, Not I BD, and MstIIA-63DA resulted in cytopathic effects after transfection; the resulting virus was termed ROka63DA. Transfection of cells with plasmid pCMV62 and cosmids VZV NotI A, Not I BD, and MstIIA-63 DB resulted in cytopathic effects after transfection; the resulting virus was termed ROka63 DB. These results indicate that ORF63 is not required for virus replication in vitro.

A rescued virus, in which the two deletions in ROka63DA were repaired, was produced by co-transfecting melanoma cells with 0.5 ug ROka63DA DNA and 1.5 ug of a VZV BclI fragment that contains ORF63 with flanking regions. At the eighth day after transfection cytopathic effects were observed, and the resulting virus was passaged in melanoma cells. After five rounds of plaque purification, in which virus clones are isolated, a "rescued" virus was isolated and termed ROka63DRA.

To verify that ROka63A, ROka63B, and ROka63DRA had the expected genome structures, Southern blotting was performed using virion DNAs. Digestion of viral DNA from VZV ROka or ROka63DRA with BamHI showed a 4.65 kb fragment, while digestion of ROka63DA or ROka63 DB showed a 3.91 kb fragment. Thus, the ORF63 deletion mutants had the expected deletions.

Immunoblotting was performed to confirm that intact ORF63 was not expressed in cells infected with ORF63 deletion mutants. Lysates from cells infected with VZV ROka or ROka63DR contained a 45 kDa ORF63 protein, while lysates from cells infected with ROka63DA or ROKa63 DB did not contain this protein. As a control, the lysates from all four virus infected cells were shown to contain similar levels of VZV gE. Therefore, cells infected with the ORF63 deletion mutants did not express ORF63 protein.

Example 3

Removal of ORF63 activity affects virus growth in cell culture. VZV growth was determined as follows. Flasks of melanoma cells were infected with 100 to 200 PFU of parental VZV, ORF63 deletion mutants, or rescued virus. At one, two, three, four, and five days after infection, cells were treated with trypsin and serial dilutions made to infect melanoma cells. One week after infection, the cells were fixed and stained with crystal violet. Virus titers were determined by counting infection-associated plaques. The peak titer of VZV ROka63DA and ROka63 DB was about ten-fold less than VZV ROka. In contrast, ROka63DR, in which the ORF63 deletions were repaired, replicated to peak titers that were similar to those of the parental virus, indicating that ORF63 helps sustain normal virus growth.

Example 4

Gene ORF63 of varicella zoster is critical to establish latent viral infection. Four to six week old female cotton rats were inoculated intramuscularly along both sides of the spine with VZV-infected melanoma cells containing $1.75 \times 10^5$ or $3.0 \times 10^5$ PFU of parental or ORF63 deletion mutant viruses. The animal protocol used has been described previously (Sato et al. 2002). Six weeks later, the animals were sacrificed and their lumbar and thoracic ganglia removed and pooled from each animal. DNA was isolated from the pooled samples and PCR was performed using 500 ng of pooled ganglia DNA and VZV primers that correspond to the ORF21 gene of VZV (Brunell et al 1999). Serial dilutions of cosmid VZV NotI A, which contains ORF21, were added to 500 ng of ganglia DNA from uninfected cotton rats and PCR was performed to generate a standard curve for estimating the numbers of latent viral DNA copies. The PCR products were resolved by electrophoresis and Southern blotting with a radiolabeled probe to ORF21 (Brunell et al 1999). Numbers of viral DNA copies were estimated by densitometry using a phosphorimager. The lower limit of detection was 10 copies of viral DNA when mixed with 500 ng of uninfected ganglia DNA.

Initially, animals were inoculated with $1.75 \times 10^5$ PFU of virus in 50 µl at 6 sites on each side of the spine intramuscularly. VZV DNA was detected in ganglia from 4 of 13 animals inoculated with VZV ROka and 0 of 10 animals infected with ROka63DA. The geometric mean number of VZV copies from PCR-positive ganglia of animals infected with VZV ROka was 48, whereas none of the animals inoculated with VZV ROka63D had detectable VZV in their ganglia.

In a comparison study, animals were similarly inoculated with $3.0 \times 10^5$ PFU of virus. VZV DNA was detected in ganglia from 8 of 12 animals inoculated with VZV ROka and 2 of 14 animals infected with ROka63DA. Accordingly, in total, VZV DNA was detected in 12 of 25 animals infected with VZV ROka and 2 of 24 infected with ROka63DA and thus VZV ORF63 is necessary for the virus to efficiently establish a latent infection.

Example 5

As described above, a VZV virus was made with just a 21 amino acid deletion in ORF63. Separately, A VZV virus "ROka63NLS" was made with the 21 amino acid deletion plus a further rearrangement in ORF62 as shown in FIG. 3. The believed gene order in 63 NLS is 60, 61, 62, 63d, 64, etc. Briefly, cells were cotransfected with a plasmid containing an NLS deletion and with VZV virion DNA from an ORF63 deletion mutant and the resulting virus was plaque purified. PCR analysis verified that all copies of ORF63 had the NLS deletion.

A rearrangement in the genome due to one copy of DNA inserting non-homologously was shown by Southern analysis and by sequencing. The sequenced region from left to right in the first IR region revealed VZV nucleotides 107,336 to 106,614 followed by 112,214-111,379 and then followed by 111,334-109,085 (nucleotide sequence numbers based on Davison and Scott). Here in this case, 107,336 to 106,614 were shown to be in the ORF62 amino portion of the protein. The ORF62 protein is between 105,204 and 109,133 and the amino portion is at 109,133. The schematic in FIG. 3, begins ORF63 in the first IR and, reading right to left, shows ORF63 followed by the region between ORF63 and ORF62, and then ORF62, wherein the sequenced portion begins, and finally ending at 106,614 of ORF62, which encodes amino acids 1-840. Accordingly, a truncated ORF62 (aa 1-840) is encoded for expression (out of 1310 total amino acids in the protein). In another embodiment, larger regions of ORF62 encoding amino acids 1 to about 900 and 1 to about of 1000 are deleted.

The region 112,214 to −111,379 encodes the portion of the VZV genome between ORFs 64 and 65, all of ORF64, and the carboxy portion of ORF63 The nucleotides 111,334 to 109,085 encode the amino portion of ORF63, the region between ORF63 and ORF62, and the amino terminus of ORF62. Accordingly, the entire ORF62 region is indicated as being encoded, followed by the region between ORF62 and ORF61, ORF61, and the other regions indicated on the schematic in FIG. 3.

Figure 4:
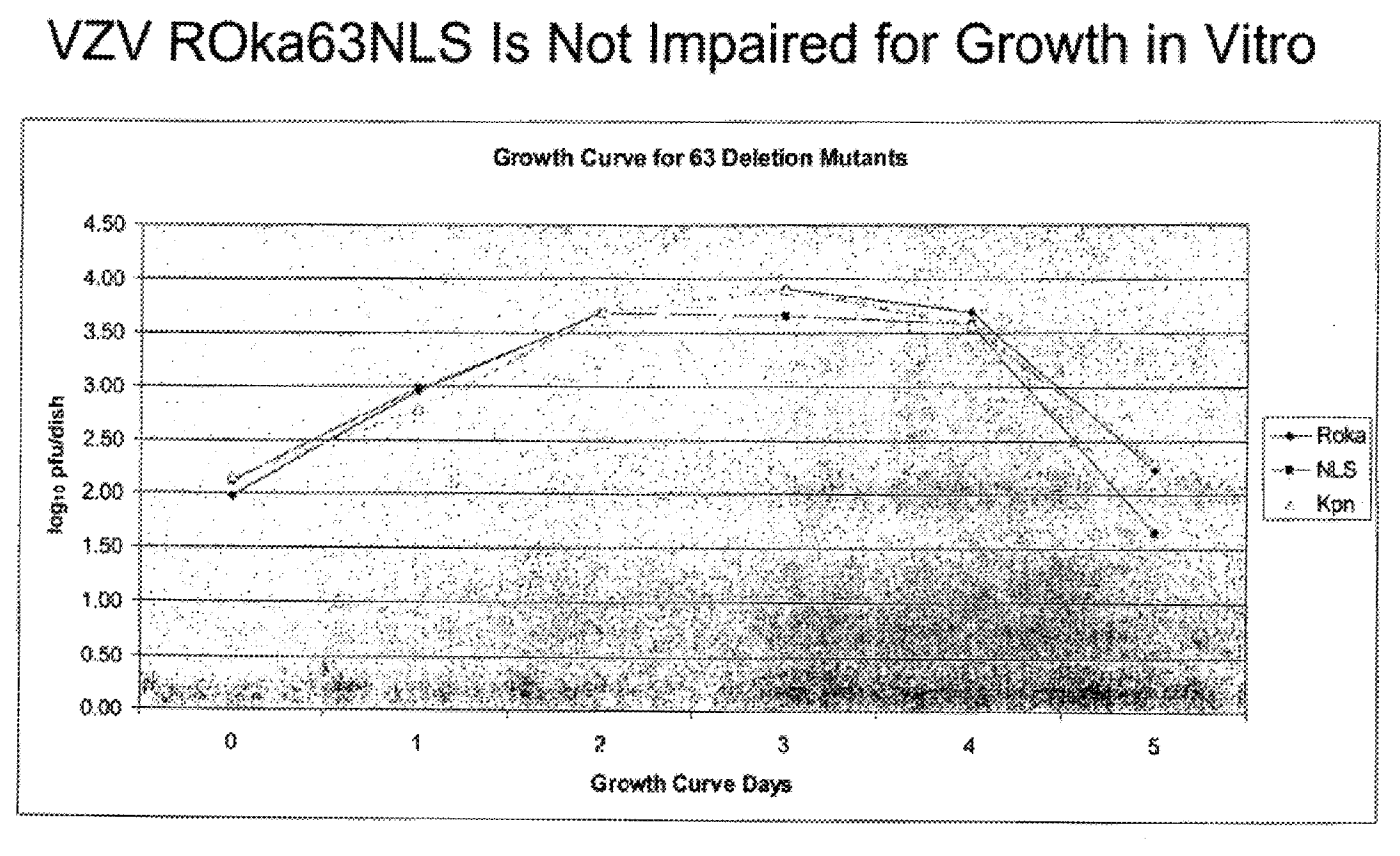
Figure 5:
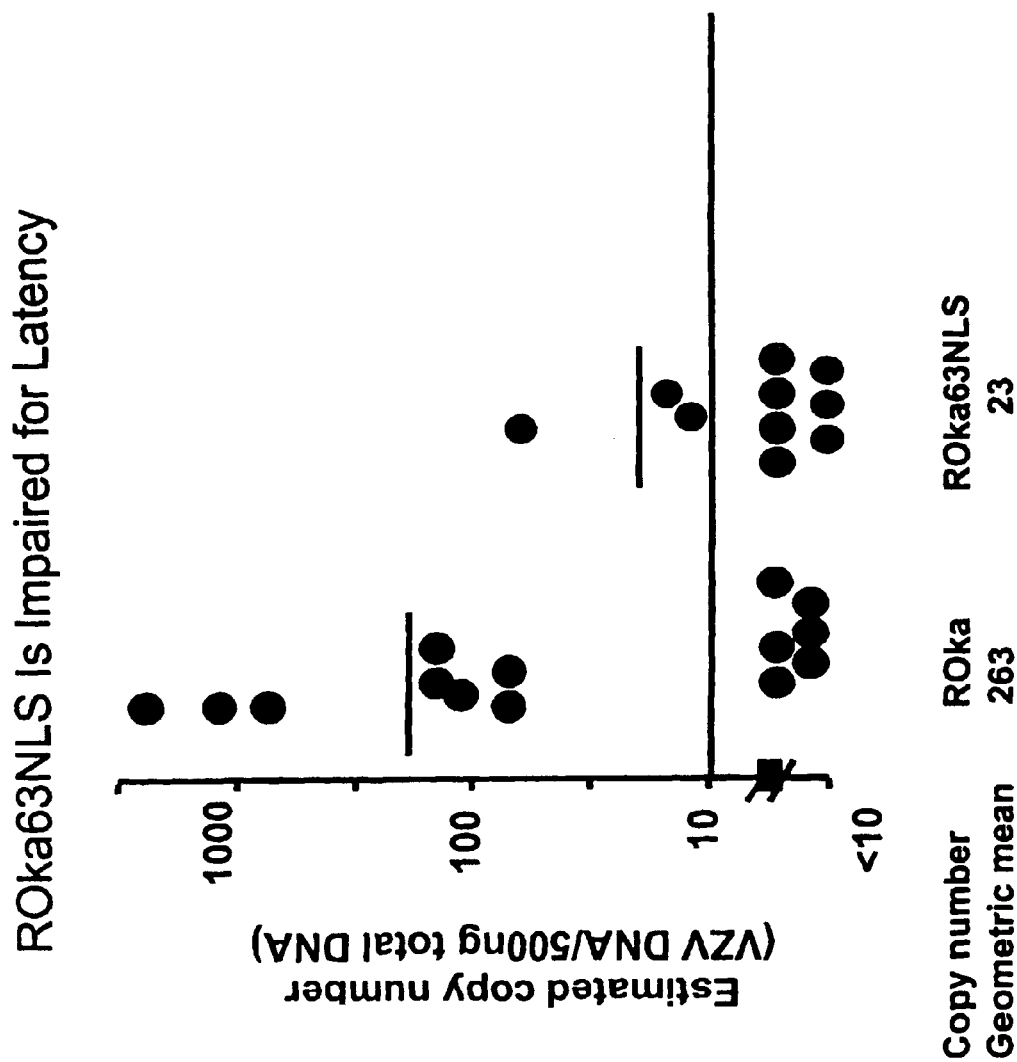
FIG. 5 is a graph that shows that ROka63NLS is impaired for latency.

The region between 111,379 and 111,334 was purposely deleted in ORF63, and encodes the nuclear localization signal of the ORF63 protein. One IR is intact, and the other IR has the insertion. The rearrangement described above may involve the second IR region, instead of the first IR region A comparison of the two viruses with wild type showed that the latter recombinant virus with the ORF62 rearrangement is impaired for latency yet grows well. See FIGS. 4 and 5.

In another embodiment, multiple strains of VZV are prepared by modifying ORF62 by rearrangements, while leaving ORF63 intact.

References

Baiker A. Bagowski C. Ito H, Sommer M, Zerboni L, Fabel K, Hay J, Ruyechan W, Arvin, A. M. J. Virol. 8(3):1181-94, 2004.

Bontems, S., Di Valentin, E., Baudoux L., Rentier, B., Sadzot-Delvaux, C., and Piette, J. Phosphorylation of varicella-zoster virus IE63 protein by casein kinase influences its cellular localization and gene regulation activity. J. Biol. Chem. 277:21050-21060, 2002.

Brunell, P. A., L. C. Ren, J. I. Cohen, S. E. Straus. 1999. Viral gene expression in rat trigeminal ganglia following neonatal infection with varicella-zoster virus. J. Med. Virol. 58:286-290.

Cohen J I, Seidel K E. Generation of varicella-zoster virus (VZV) and viral mutants from cosmid DNAs: VZV thymidylate synthetase is not essential for replication in vitro. Proc. Natl. Acad. Sci. USA 1993; 90:7376-7380.

Cohrs R. J., J. Randall, J. Smith, D. H. Gilden, C. Dabrowski, H. van der Keyl, R. Tal-Singer. 2000. Analysis of individual human trigeminal ganglia for latent herpes simplex virus type 1 and varicella-zoster virus nucleic acids using real time PCR. J. Virol 74:11464-11471.

Davison A J, Scott J. The complete DNA sequence of varicella-zoster virus. J. Gen. Virol. 1986; 67:1759-1816.

Debrus S, Sadzot-Delvaux C, Nikkels A F, Piette J, Rentier B. Varicella-zoster virus gene 63 encodes an immediate-early protein that is abundantly expressed during latency. J. Virol. 1995; 69:3240-3245.

Fuchs, W., Ehrlich, C., Klupp, B. G., and T. C. Mettenleiter, 2000. Characterization of the replication origin ($Ori_s$) and adjoining parts of the inverted repeat sequences of the pseudorabies virus genome J. Gen. Virol. 81: 1539-1543.

Ghiasi. H, Osorio, Y, Perng, G. C., Nesburn, A. B., and S. L. Wechsler, 2002. Overexpression of interleukin-2 by a recombinant herpes simplex virus type 1 attenuates pathogenicity and enhances antiviral immunity. J. Virol. 76: 9069-9078.

Heineman T C, Cohen J I. The varicella-zoster virus (VZV) open reading frame 47 (ORF47) protein kinase is dispensable for viral replication and is not required for phosphorylation of ORF63 protein, the VZV homolog of herpes simplex virus ICP22. J. Virol. 1995; 69:7367-7370.

Kennedy P. G. E., E. Grinfeld, J. E. Bell. 2000. Varicella-zoster virus gene expression in latently infected and explanted human ganglia. J. Virol. 74:11893-11898.

Kennedy P. G. E., E. Grinfeld, S. Bontems, C. Sadzot-Delvaux. 2001. Varicella-zoster virus gene expression in latently infected rat dorsal root ganglia. Virology 289:218-223.

Kenyon, T. K., Lynch, J., Jay, J, Ruyechan, W., & Grose, C. (2001) Varicella-zoster virus ORF47 protein serine kinase: characterization of a cloned, biologically active phosphotrasnferase and two viral substrates, ORF62 and ORF63. J. Virol. 75, 8854-88858.

Kinchington P R, Bookey D, Turse S E. The transcriptional regulatory proteins encoded by varicella-zoster virus open reading frames (ORFs) 4 and 63, but not ORF61 are associated with purified virus particles. J. Virol. 1995; 69:4274-4282.

Leong, K. H., Ramsay, A. J., Boyle, D. B., and I. A. Ramshaw, 1994. Selective induction of immune responses by cytokines coexpressed in recombinant fowlpox virus. J. Virol. 68: 8125-8130.

Lungu, O., C. A. Panagiotidis, P. W. Annunziato, A. A. Gershon, S. J. Silverstein. 1998. Aberrant intracellular localization of varicella-zoster virus regulatory proteins during latency. Proc. Natl. Acad. Sci. USA 95:7080-7085.

Mahalingam R, M. Wellish, R. Cohrs, S. Debrus, J. Pietta, B. Rentier, et al. 1996. Expression of protein encoded by varicella-zoster virus open reading frame 63 in latently infected human ganglionic neurons. Proc. Natl. Acad. Sci. USA 93:2122-2124.

Ng T I, Keenan L, Kinchington P R, Grose C. 1994. Phosphorylation of varicella-zoster virus open reading frame (ORF) 62 regulatory product by viral ORF47-associated protein kinase. J. Virol. 68:1350-1359.

Parcells, M. S., A. S. Anderson, J. L. Cantello and R. W. Morgan. 1994. Characterization of Marek's disease virus insertion and deletion mutants that lack US1 (ICP22 homolog), US10, and/or US2 and neighboring short component open reading frames. J. Virol. 68: 8239-8253.

Ramsay, A. J., Leong, K. H., Boyle, D., Ruby, J. and I. A. Ramshaw, 1994. Enhancement of mucosal IgA responses by interleukins 5 and 6 encoded in recombinant vaccine vectors. Reprod. Fertil. Dev. 6: 389-392.

Sato H, Callanan L D, Pesnicak L, Krogmann T, Cohen J I. 2002. Varicella-zoster virus (VZV) ORF17 protein induces RNA cleavage and is critical for replication of VZV at 37° C., but not 33° C. J. Virol. 76:11012-11023.

Sadzot-Delvaux, C. S. Debrus, A. Nikkels, J. Piette, B. Rentier. 1995. Varicella-soter virus latency in the adult rat is a useful model for human latent infection. Neurology 45 (Suppl 8):S18-S20.

Sharrar R G, LaRussa P, Steinberg S A, Steinberg S P, Sweet A R, Keatley R M, Wells M E, Stephenson W P, Gershon A A. The postmarketing safety profile of varicella vaccine. Vaccine. 2000 Nov. 22; 19(7-8):916-23.

Sommers M, Zagha E, Serrano O K, Ku C C, Zerboni L, Baiker A, Santos R, Spengler M, Lynch J, Grose C, Ruyechan W, Hay J, Arvin A M. Mutational analysis of the repeated open reading frames, ORFs63 and 70 and ORFs64 and 69. J. Virol. 2001; 75:8224-8239.

Stevenson D, Xue M, Hay J, Ruyechan W T. Phosphorylation and nuclear localization of the varicella-zoster virus gene 63 protein. J. Virol. 1996; 70:658-662.

Wise R P, Salive M E, Braunn M M, Mootrey G T, Seward J F, Rider L G, and P. R. Krause. Postlicensure safety surveillance for varicella vaccine. J.A.M.A. 2000 Sep. 13; 284(10):1271-9.

Xia, D., Srinivas, S., Sato, H., Pesnicak, L., Straus, S. E., and J. I. Cohen. Varicella-zoster virus ORF21, which is expressed during latency, is essential for virus replication but dispensable for establishment of latency. J. Virol. 2003, in press.

The description, specific examples and data, while indicating exemplary embodiments, are given by way of illustration and are not intended to limit the invention. Various changes and modifications will become apparent to the skilled artisan from this disclosure and are included within the ambit of the invention. The references cited above and throughout this disclosure are herein incorporated by reference in their entireties.

We claim:

1. A live varicella-zoster virus vaccine, the vaccine having impaired ability to establish latency, comprising: a recombinant varicella-zoster virus that has at least one intact ORF62 gene, and at least one additional copy of a ORF62 gene that has a deletion, wherein the deletion comprises at least the portion of ORF62 that encodes the carboxy-terminal 470 amino acids of the ORF62 polypeptide.

2. The vaccine of claim 1, wherein the recombinant virus further substantially lacks a gene or a portion of a gene selected from the group consisting of the ORF63 gene of varicella-zoster virus and the ORF70 gene of varicella-zoster virus.

3. The vaccine of claim 1, wherein the recombinant virus is impaired for latency but replicates to wild-type titers.

4. A live varicella-zoster virus vaccine, the vaccine having impaired ability to establish latency, comprising: a recombinant varicella-zoster virus that has at least one intact ORF62 gene but that contains another copy of a ORF62 that has a deletion, wherein the deletion comprises at least the portion of ORF62 that encodes the carboxy-terminal 470 amino acids of the ORF62 polypeptide.

5. The vaccine of claim 4, wherein the recombinant varicella-zoster virus further substantially lacks a gene or a portion of a gene selected from the group consisting of the ORF63 gene of varicella-zoster virus and the ORF70 gene of varicella-zoster virus.

6. A vaccine as described in claim 1, wherein the deletion is within the carboxyl terminal half of the protein coding sequence.

7. The vaccine of claim 4, wherein the deletion is within the carboxyl terminal half of the protein coding sequence of ORF62.

\* \* \* \* \*

SEQUENCE LISTING

```
<160> NUMBER OF SEQ ID NOS: 18

<210> SEQ ID NO 1
<211> LENGTH: 131
<212> TYPE: PRT
<213> ORGANISM: Artificial Sequence
<220> FEATURE:
<223> OTHER INFORMATION: Description of Artificial Sequence: Synthetic
      peptide consensus sequence

<400> SEQUENCE: 1

His Pro Glu Tyr Gly Ser Ala Pro Ser Pro Glu Asp Val Arg Leu Glu
  1               5                  10                  15

Arg Gly Pro Gly Ala Phe Cys Ala Pro Pro Trp Arg Pro Asp Val Ala
             20                  25                  30

Arg Leu Ser Glu Asp Thr Asn Lys Leu Phe Arg Cys Ile Ala Thr Ser
         35                  40                  45

Ser Leu Asn Val Thr Pro Asp Ser Arg Ala Leu Arg Arg Ala Leu Leu
     50                  55                  60

Asp Phe Tyr Met Met Gly Arg Thr Gly Gln Arg Pro Thr Arg Ala Cys
 65                  70                  75                  80

Trp Glu Thr Leu Leu Gln Leu Ser Pro Glu Gln Ser Arg Pro Leu Arg
                 85                  90                  95

Arg Thr Leu Arg Glu Val Asn Arg Arg Ser Pro His Asp Arg Ser Phe
            100                 105                 110

Leu Tyr Pro Pro Pro Asp Ile Pro Pro Pro Leu Phe Ala Leu Glu Cys
        115                 120                 125

Asp Val Ser
    130

<210> SEQ ID NO 2
<211> LENGTH: 132
<212> TYPE: PRT
<213> ORGANISM: Varicella zoster virus

<400> SEQUENCE: 2

Lys Met Glu Tyr Gly Ser Ala Pro Gly Pro Leu Asn Gly Arg Asp Thr
  1               5                  10                  15

Ser Arg Gly Pro Gly Ala Phe Cys Thr Pro Gly Trp Glu Ile His Pro
             20                  25                  30

Ala Arg Leu Val Glu Asp Ile Asn Arg Val Phe Leu Cys Ile Ala Gln
         35                  40                  45

Ser Ser Gly Arg Val Thr Arg Asp Ser Arg Arg Leu Arg Arg Ile Cys
     50                  55                  60

Leu Asp Phe Tyr Leu Met Gly Arg Thr Arg Gln Arg Pro Thr Leu Ala
 65                  70                  75                  80

Cys Trp Glu Glu Leu Leu Gln Leu Gln Pro Thr Gln Thr Gln Cys Leu
                 85                  90                  95

Arg Ala Thr Leu Met Glu Val Ser His Arg Pro Pro Arg Gly Glu Asp
            100                 105                 110

Gly Phe Ile Glu Ala Pro Asn Val Pro Leu His Arg Ser Ala Leu Glu
        115                 120                 125

Cys Asp Val Ser
    130

<210> SEQ ID NO 3
<211> LENGTH: 133
<212> TYPE: PRT
```

<213> ORGANISM: Feline herpesvirus 1

<400> SEQUENCE: 3

His Pro Glu Tyr Gly Ser Val Val Ala Ser Arg Asp Leu Arg Ala Tyr
1               5                   10                  15

Leu Thr His Gly Pro Gly Ala Phe Cys Ser Pro Pro Trp Arg Cys Asp
            20                  25                  30

Leu Lys Arg Leu Met Lys Asp Val Asn Ile Met Phe Arg Cys Ile Ala
        35                  40                  45

Thr Ser Ser Val Asn Val Ser Ser Asp Ser Arg Ala Leu Arg Arg Ala
    50                  55                  60

Leu Leu Asp Phe Tyr Ile Met Gly Tyr Thr Asn Gln Arg Pro Thr Arg
65                  70                  75                  80

Ala Cys Trp Glu Thr Leu Leu Gln Leu Ser Ser Glu Gln Ala Arg Pro
                85                  90                  95

Leu Arg Ala Thr Leu Arg His Leu Asn Thr Thr Glu Pro Cys Asp Arg
            100                 105                 110

Arg Phe Leu Glu Pro Pro Thr Gln Val Pro Pro Ile Leu Phe Gly Gln
        115                 120                 125

Glu Cys Asp Val Ser
    130

<210> SEQ ID NO 4
<211> LENGTH: 130
<212> TYPE: PRT
<213> ORGANISM: Marek's disease virus

<400> SEQUENCE: 4

His Pro Glu Tyr Gly Ser Asp Ser Ser Asp Gln Asp Phe Glu Leu Asn
1               5                   10                  15

Asn Val Gly Lys Phe Cys Pro Leu Pro Trp Lys Pro Asp Val Ala Arg
            20                  25                  30

Leu Cys Ala Asp Thr Asn Lys Leu Phe Arg Cys Phe Ile Arg Cys Arg
        35                  40                  45

Leu Asn Ser Gly Pro Phe His Asp Ala Leu Arg Arg Ala Leu Phe Asp
    50                  55                  60

Ile His Met Ile Gly Arg Met Gly Tyr Arg Leu Lys Gln Ala Glu Trp
65                  70                  75                  80

Glu Thr Ile Met Asn Leu Thr Pro Arg Gln Ser Leu His Leu Arg Arg
                85                  90                  95

Thr Leu Arg Asp Ala Asp Ser Arg Ser Ala His Pro Ile Ser Asp Ile
            100                 105                 110

Tyr Ala Ser Asp Ser Ile Phe His Pro Ile Ala Ala Ser Ser Gly Thr
        115                 120                 125

Ile Ser
    130

<210> SEQ ID NO 5
<211> LENGTH: 130
<212> TYPE: PRT
<213> ORGANISM: Laryngotracheitis virus

<400> SEQUENCE: 5

His Asp Glu Tyr Gly Gln Ile Ser Leu Gly Ser Pro Val Glu Ser Ser
1               5                   10                  15

Asn Ser Thr Gly Asn Phe Cys Ala Pro Pro Trp Met Pro Asp Ile Pro
            20                  25                  30

```
Arg Leu Ser Asn Asp Thr Cys Lys Ile Phe Arg Cys Leu Thr Ser Cys
         35                  40                  45

Arg Leu Asn Cys Ala Pro Phe His Asp Ala Leu Arg Arg Ala Leu Leu
     50                  55                  60

Asp Met His Met Leu Gly Arg Met Gly Phe Arg Leu Arg Gln His Glu
 65                  70                  75                  80

Trp Glu Arg Ile Met Gln Leu Thr Pro Asp Glu Ser Ile Asn Leu Arg
                 85                  90                  95

Arg Thr Leu Leu Glu Ala Asp Glu Arg Ser Ser His Cys Met Pro Asn
             100                 105                 110

Val Tyr Ala Ser Asp Ile Ser Asn Ser Leu Glu Ala Gly Thr Met Gln
         115                 120                 125

Val Thr
    130

<210> SEQ ID NO 6
<211> LENGTH: 130
<212> TYPE: PRT
<213> ORGANISM: Meleagrid herpes virus 1

<400> SEQUENCE: 6

Asn Glu Asp Cys Asp Glu Asn Val Thr Ile Asp Gly Ile Gly Glu Glu
  1               5                  10                  15

Tyr Ala Gln Phe Phe Met Ser Pro Gln Trp Val Pro Asn Leu His Arg
                 20                  25                  30

Leu Ser Glu Asp Thr Lys Lys Val Tyr Arg Cys Met Val Ser Asn Arg
         35                  40                  45

Leu Asn Tyr Phe Pro Tyr Tyr Glu Ala Phe Arg Arg Ser Leu Phe Asp
     50                  55                  60

Met Tyr Met Leu Gly Arg Leu Gly Arg Arg Leu Lys Arg Ser Asp Trp
 65                  70                  75                  80

Glu Thr Ile Met His Leu Ser Pro Thr Gln Ser Arg Arg Leu His Arg
                 85                  90                  95

Thr Leu Arg Phe Val Glu Arg Arg Ile Ile Pro Ser Asn Ser Tyr Ile
             100                 105                 110

Arg Thr Ser Gly His Val Pro Pro Ser Arg Ala Leu Pro Thr Asp Thr
         115                 120                 125

Asn Leu
    130

<210> SEQ ID NO 7
<211> LENGTH: 128
<212> TYPE: PRT
<213> ORGANISM: Bovine herpesvirus 1

<400> SEQUENCE: 7

Arg Val Val Ser Gly Pro Ala Pro Ala Asp Glu His Ala Arg Arg Gly
  1               5                  10                  15

Pro Gly Ala Phe Cys Pro Glu Asp Trp Arg Pro Glu Ala Leu Arg Leu
                 20                  25                  30

Ala Ile Asp Val Asn Thr Leu Phe Arg Cys Ile Ala Thr Gly Ser Ala
         35                  40                  45

Phe Val Thr Ala Asp Thr Arg Ala Leu Arg Arg Ala Leu Val Gly Phe
     50                  55                  60

Phe Leu Leu Gly Tyr Thr Gly Ala Thr Pro Thr Asp Ala Cys Trp Glu
 65                  70                  75                  80
```

```
Ala Leu Leu Gln Leu Ser Pro Glu Gln Ala Gly Pro Leu Arg Arg Leu
                85                  90                  95

Leu Arg Ala Ala Ala Ala Gly Pro Arg Ala Arg Pro Leu Ser Pro
            100                 105                 110

Pro Ala Arg Leu Pro Gly Pro Leu Phe Gly Ala Glu Cys Asp Val Ser
            115                 120                 125
```

<210> SEQ ID NO 8
<211> LENGTH: 133
<212> TYPE: PRT
<213> ORGANISM: Equine herpesvirus 1

<400> SEQUENCE: 8

```
His Pro Glu Tyr Gly Met Pro Leu Ser Pro Arg Ala Leu Arg Pro Tyr
  1               5                  10                  15

Leu Ala Arg Gly Pro Gly Ala Phe Cys Ala Pro Pro Trp Arg Pro Asp
             20                  25                  30

Val Asn Arg Leu Ala Gly Asp Val Asn Arg Leu Phe Arg Gly Ile Ser
             35                  40                  45

Thr Ser Ser Ile His Val Thr Glu Asp Ser Arg Thr Leu Arg Arg Ala
 50                  55                  60

Leu Leu Asp Phe Tyr Ala Met Gly Tyr Thr His Thr Arg Pro Thr Leu
 65                  70                  75                  80

Glu Cys Trp Gln Ser Leu Leu Gln Leu Pro Glu Gln Ser Phe Pro
                85                  90                  95

Leu Arg Ala Thr Leu Arg Ala Leu Asn Ser Gly Asp Arg Tyr Glu Gln
            100                 105                 110

Arg Phe Leu Glu Pro Pro Ser Asp Pro Pro Asn Thr Leu Phe Gly Glu
            115                 120                 125

Glu Cys Asp Val Ser
            130
```

<210> SEQ ID NO 9
<211> LENGTH: 132
<212> TYPE: PRT
<213> ORGANISM: Pseudorabies virus

<400> SEQUENCE: 9

```
His Pro Glu Tyr Gly Pro Pro Asp Pro Glu Glu Val Arg Val His
  1               5                  10                  15

Gly Ala Arg Gly Pro Gly Ala Phe Cys Ala Ala Pro Trp Arg Pro Asp
             20                  25                  30

Thr Arg Arg Leu Gly Ala Asp Val Asn Arg Leu Phe Arg Gly Ile Ala
             35                  40                  45

Val Ser Ala Ala Asp Val Thr Gly Asp Thr Arg Ala Leu Arg Arg Ala
 50                  55                  60

Leu Phe Asp Phe Tyr Ala Met Gly Tyr Thr Arg Gln Arg Pro Ser Ala
 65                  70                  75                  80

Pro Cys Trp Gln Ala Leu Leu Gln Leu Ser Pro Glu Gln Ser Ala Pro
                85                  90                  95

Leu Arg Ser Ala Leu Arg Glu Leu Asn Glu Arg Asp Tyr Asp Pro
            100                 105                 110

Arg Val Leu Ser Pro Pro Val Ile Glu Gly Pro Leu Phe Gly Glu Glu
            115                 120                 125

Cys Asp Val Asp
            130
```

<210> SEQ ID NO 10
<211> LENGTH: 131
<212> TYPE: PRT
<213> ORGANISM: Simian varicella virus

<400> SEQUENCE: 10

Ala Arg Glu Tyr Gly Ser Val Thr Pro Gly Leu His Ser Asn Asp Leu
 1               5                   10                  15

Glu His Gly Pro Gly Ala Phe Cys Ala Pro Pro Trp Ser Leu Asp Val
            20                  25                  30

Ala Arg Leu Val Lys Asp Ile Asn Arg Met Phe Leu Cys Ile Ala Arg
        35                  40                  45

Ala Ser Gly Arg Val Thr Arg Asp Ser Arg Thr Leu Arg Arg Ile Cys
    50                  55                  60

Val Asp Phe Tyr Leu Met Gly Arg Leu Lys Gln Arg Pro Thr Val Thr
65                  70                  75                  80

Cys Trp Glu Glu Leu Leu Gln Leu Gln Pro Thr Gln Thr Arg Cys Leu
                85                  90                  95

Arg Ala Thr Leu Ala Asp Val Ala Arg Arg Ser Pro Ile Thr Glu Glu
            100                 105                 110

Phe Ile Asp Pro Pro Asp Ile Pro Leu His Arg Ile Ala Leu Glu Cys
        115                 120                 125

Asp Val Ser
    130

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctagttggcc gcggcggcct ccc                                            23

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaggccgc cgcggccaa                                                 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aattgtaggc cgccgcggcc a                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agcttggccg cggcggccta c                                              21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccggagagcc taggagact                                                 19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccggagtctc ctaggctct                                                 19

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Arg Arg Arg
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Lys Lys Lys
  1